United States Patent [19]

Niznik

[11] 4,097,425
[45] Jun. 27, 1978

[54] THERMOPLASTIC FORMABLE BLENDS, A FOAMING METHOD AND PRODUCTS MADE THEREBY

[75] Inventor: George E. Niznik, Elnora, N.Y.

[73] Assignee: General Electric Company, Schenectady, N.Y.

[21] Appl. No.: 669,028

[22] Filed: Mar. 22, 1976

Related U.S. Application Data

[63] Continuation-in-part of Ser. No. 608,451, Aug. 28, 1975, abandoned.

[51] Int. Cl.$^2$ .............................. C08J 9/08; C08J 9/10
[52] U.S. Cl. .............................. 260/2.5 N; 260/2.5 R; 260/2.5 HB; 260/2.5 HA; 260/2.5 P; 260/37 PC; 260/860; 260/873; 544/68
[58] Field of Search .................. 260/2.5 HA, 2.5 HB, 260/2.5 N; 544/68

[56] References Cited

U.S. PATENT DOCUMENTS 3,779,954  12/1973  Wirth et al. ..................... 260/2.5 HB
3,781,233  12/1973  Muller et al. .................. 260/2.5 HB

OTHER PUBLICATIONS

M. Rosenblum et al., "Synthesis of Dihydrooxadiazinones," JACS vol. 85, p. 3874, (1963).

Primary Examiner—Morton Foelak
Attorney, Agent, or Firm—William A. Teoli; Joseph T. Cohen; Charles T. Watts

[57] ABSTRACT

Foamable blends are provided of high performance thermoplastic polymers such as polycarbonates, polyesters, etc., and an effective amount of a dihydrooxadiazinone blowing agent. The blends can be melt extruded into pellets and sheet and converted into thermoplastic foam structures in accordance with conventional injection molding techniques.

32 Claims, No Drawings

THERMOPLASTIC FORMABLE BLENDS, A FOAMING METHOD AND PRODUCTS MADE THEREBY

This application is a continuation-in-part of Serial No. 608,451, now abandoned, filed August 28, 1975 and assigned to the same assignee as the present invention.

The present invention relates to thermoplastic blends of a thermoplastic organic polymer and a dihydrooxadiazinone. More particularly, the present invention relates to foamable compositions, a method for making a thermoplastic foam and foamed structures made therefrom.

Prior to the present invention, the plastics industry expended considerable effort towards the study and development of high performance theremoplastic foams for the purpose of making lightweight structural substitutes for metal in various applications such as used in the automotive industry. As shown by Hunter et al., U.S. Pat. No. 3,888,801, hydrazodicarboxylates have commonly been employed as blowing agents for various thermoplastic organic polymers for the purpose of reducing the overall weight of particular thermoplastic materials when molded to a specific shape. Other blowing agents, which are commonly used with various thermoplastic organic polymers, are 5-phenyltetrazole, benzamides, etc., as shown by Muller et al, U.S. Pat. No. 3,781,233, and Wirth et al, U.S. Pat. No. 3,779,954. Although hydrazodicarboxylates, such as diisopropyl hydrazodicarboxylate and 5-phenyltetrazole have been found effective for reducing the density of various thermoplastic organic polymers, such as polycarbonates, polyesters, polyacrylates, etc., it has been shown that a significant degree of polymer degradation can occur during the foaming process. Polymer degradation is generally evidenced by a reduction in the intrinsic viscosity of the polymer when a comparison of polymer intrinsic viscosity is made before and after foaming. Polymer degradation is also directly related to reduction in foam impact strength.

Although it is not completely understood, one possible explanation as to why blowing agents, such as the above-described hydrazodicarboxylates can cause a significant degree of polymer degradation upon foaming, is that such blowing agents have decomposition by products such as aliphatic alcohols, ammonia, water, etc.

Blowing agents such as the above-described benzazimides and bisbenzazimides are also polymer degradation prone, since water is a decomposition byproduct. Those skilled in the art know that careful drying of high performance thermoplastics, such as polycarbonates, is required prior to molding because of possible risk of polymer degradation. It would be desirable, therefore, to provide blowing agents which can be employed in a variety of high performance thermoplastic organic polymers, such as polyesters, polycarbonates, etc., which do not degrade the thermoplastic polymer and which resist an adverse reduction in impact strength of the foam product beyond that normally expected from the change in the density of the material as the result of foaming.

The present invention is based on the discovery that certain heat unstable organic diazacyclic compounds having maximum decomposition rates at temperatures in the range of between 170° C to 310° C, and more particularly, dihydrooxadiazinones, some of which are shown by M. Rosenblum et al., J. Amer. Chem. Soc., 85, 3874 (1963), can be employed in a variety of organic thermoplastic polymers such as polycarbonates, polyesters, and others more particularly defined hereinafter to produce blends which can be injection molded to various foamed shapes without effecting a significant change in organic polymer intrinsic viscosity or suffer a more than normal reduction in impact strength of the foamed structure. Some of the dihydrooxadiazinones which can be used in the practice of the present invention are shown and can be made by methods described in my copending application Ser. No. 608,540, filed Aug. 28, 1975 and assigned to the same assignee as the present invention. Additional dihydrooxadiazinones and methods for making are described by Rosenblum et al as indicated above.

There is provided by the present invention, substantially uniform injection moldable blends comprising a thermoplastic organic polymer, and 0.1 to 25 percent of the blend of a dihydrooxadiazinone blowing agent which blend is convertible to a substantially uniform thermoplastic foam by conventional injection molding conditions or usable as a concentrate to make an injection moldable blend convertible to a foam.

Included by the dihydrooxadiazinones which can be employed in making the blends of the present invention are compounds having the formula

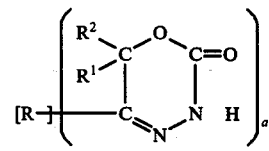

where "a" is an integer equal to 1 or 2, R is a monovalent radical when "a" is 1, and a divalent radical when "a" is 2, selected from a $C_{(1-8)}$ alkyl radical or alkylene radical, a $C_{(6-30)}$ aryl radical or arylene radical and halogenated derivatives thereof. $R^1$ and $R^2$ are the same or different monovalent radicals selected from hydrogen, $C_{(1-8)}$ alkyl, alkylene, $C_{(6-30)}$ aryl, alkoxy, aryloxy and where $R^1$ and $R^2$ are both alkyl, they can be part of a cycloaliphatic ring structure.

Radicals included by R of Formula 1 are $C_{(1-8)}$ alkyl radicals, such as methyl, ethyl, propyl, butyl, etc.; aryl radicals such as phenyl, tolyl, xylol, napthyl, anthryl, etc.; halo alkyls such as chloroethyl, trifluoropropyl, etc.; halo aryls such as chlorophenyl, bromotolyl, etc.; nitro aryls and sulfoaryls. Radicals included by $R^1$ and $R^2$ are hydrogen, and $C_{(1-8)}$ alkyl radicals such as methyl, ethyl, propyl, etc.; alkoxy radicals such as methoxy, ethoxy, propoxy, butoxy, etc.; aryloxy radicals such as phenoxy, cresoxy, napthoxy, etc. In particular instances where $R^1$ and $R^2$ are both alkyl they can be part of a cycloaliphatic ring structure such as cyclopentyl, cyclohexyl, cycloheptyl. In other situations where $R^1$ and $R^2$ are both aryl, they can be phenyl, tolyl, xylyl, napthyl, anthryl, or a mixture of any two of the aforementioned aryl radicals.

Some of the dihydrooxadiazinones which can be used in the practice of the invention are, for example, 5,6-dimethyl-3,6-dihydro-1,3,4-oxadiazin-2-one
5,6,6-trimethyl-3,6-dihydro-1,3,4-oxadiazin-2-one
5-ethyl-6-methoxy-3,6-dihydro-1,3,4-oxadiazin-2-one
5,6-diphenyl-3,6-dihydro-1,3,4-oxadiazin-2-one 5-(p-bromophenyl)-3,6-dihydro-1,3,4-oxadiazin-2-one
5-phenyl-6-methyl-3,6-dihydro-1,3,4-oxadiazin-2-one
5,6-bis(p-methoxyphenyl)-3,6-dihydro-1,3,4-oxadiazin-2-one
5-naphthyl-3,6-dihydro-1,3,4-oxadizain-2-one
5-(o,o,p-tribromophenyl)-6-propyl-3,6-dihydro-1,3,4-oxadiazin-2-one
5-(p-hydroxyphenyl)-3,6-dihydro-1,3,4-oxadizain-2-one
5-phenyl-6,6-cyclopentylene-3,6-dihydro-1,3,4-oxadiazin-2-one
5-(m-nitrophenyl)-3,6-dihydro-1,3,4-oxadiazin-2-one
5-(p-benzenesulfonic acid sodium salt)-3,6-dihydro-1,3,4-oxadiazin-2-one
5-(2-fluorenyl)-6-trifluoroethyl-3,6-dihydro-1,3,4-oxadiazin-2-one
5-phenyl-6-(cyanophenylmethyl)-3,6-dihydro-1,3,4-oxadiazin-2-one
5-phenyl-6-cyano-6-methyl-3,6-dihydro-1,3,4-oxadiazin-2-one and such polycyclic formulas resulting from divalent substitution as

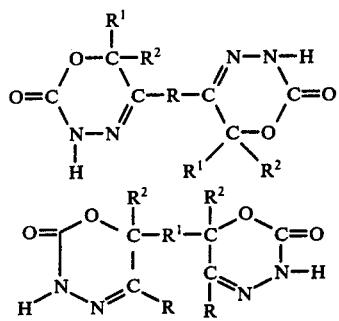

Included by the term "thermoplastic organic polymer" which can be used in the practice of the invention includes, for example, any organic polymer which can be injection molded at least twice at a temperature in the range of from 150° C to 400° C such as polycarbonates, polyesters, such as polybutylene terephthalate, polyethylene terephthalate, polybutylene-terephthalate-polybutyleneoxide copolymers, etc., poly(4,4-cyclohexylidenediphenylene isophthalate), poly(4,4-isopropylidenediphenylene isophthalate), poly(-p-hydroxybenzoic acid), polyolefins such as poly(hexafluoropropylene), polypropylene, polyacrylates and polymethacrylates, polystyrenes such as polystyrene, poly(4-tert-butylstyrene), poly(4-bromostyrene), poly(α-methylstyrene), polyamides such as polycaprolactam and poly-hexamethyleneadipamide, polyvinylchloride, polyphenylene oxide based resins, including blends with polystyrene, polyarylsulfones, ABS polymers, polystyreneacrylonitrile copolymers, polyacetals, urethane elastomers, polyphenylene sulfide, polymides, polysilphenylenes; also various copolymers, block copolymers, polymer blends and alloys of the components mentioned above.

In the practice of the invention, the thermoplastic blends can be made in the form of a dry powder, in an extruded pelletized form, in the form of an extruded thermoplastic sheet, etc., based on the melt characteristics of the thermoplastic organic polymer and the decomposition temperature of the blowing agent. In instances where the decomposition temperature of the blowing agent, which hereinafter will be used interchangeable with the term "dihydrooxadiazinone", as defined above, is below or about the temperature at which the thermoplastic organic polymer can be melt extruded or slightly above, it is preferred to make the thermoplastic blend in the form of a dry powder. Blowing agents exhibiting maximum decomposition rates at temperatures at least 25° C greater than the melt extrusion temperature of the thermoplastic organic polymer can provide for extrudable foamable blends or concentrates, having from about 1% to 25% by weight or more of blowing agent based on the weight of blowing agent and thermoplastic organic polymer, can be further melt extruded with additional thermoplastic organic polymer to make foamable compositions. Melt extruded pellets or sheets having from about 0.1 to 1.0% by weight of dihydroxadiazinone, can be converted to foam structures at higher injection molding temperatures. Preferably, the decomposition temperatures of the blowing agents used in the practice of the present invention to make foamable thermoplastic blends have maximum decomposition rates in the range of between about 170° C to 310° C. A particular preferred combination of blowing agent and thermoplastic organic polymer either in the form of a concentrate or foamable blend is a combination of a polycarbonate resin, referred to commercially as LEXAN® polycarbonate resin, a trademark of the General Electric Company with 5-phenyl-3,6-dihydrol-1,3,4-oxadiazin-2-one as a blowing agent. A class of preferred thermoplastic organic blends convertible to high performance foams in accordance with the practice of the invention utilized high performance thermoplastic organic polymer in combination with a dihydrooxadiazinone of the formula,

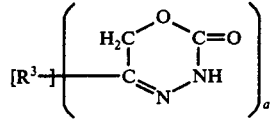

where $R^3$ is a monovalent or divalent C (6-30) aryl radical within the scope of dihydrooxidiazinones, as previously defined. Preferred blends can be in the form of a powder, pellet or sheet with an organic polymer selected from a polycarbonate, polyphenylene oxide, polyphenylene oxide-polystyrene blends, polyarylsulfone, polyimide and polycarbonate polymers resulting from the phosgenation or ester interchange of 1,1-dichloro-2,2-bis(4-hydroxyphenyl)ethylene, or polyesters derived from such dihydricphenol, as well as polyamides, etc. The latter thermoplastic organic polymers which are based on the use of 1,1-dichloro-2,2-bis(4-hydroxyphenyl)ethylene can provide for the production of high performance thermoplastic foams. An example of the use of such chloral derived dihydric phenol is shown by Zbigniew Dobkowski et al., Synthesis of Polycarbonates by Interfacial Method, Polymery-Tworzywa Wielkocasteczkowe (1970).

Another preferred thermoplastic foamable blend which can be employed in the practice of the invention is based on the use of 3,6-dihydro-5,6-diphenyl-1,3,4-oxadiazin-2-one, reported by M. Rosenblum et al., Chemistry and Industry, Page 1480 (December 15, 1956), which is shown as follows:

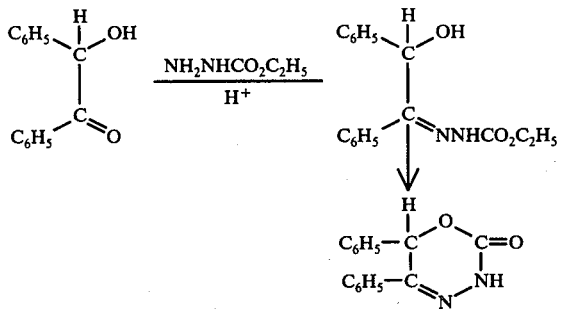

The diphenyl substituted dihydrooxidiazinone is preferably utilized in combination with any one or more of the aforementioned thermoplastic organic polymers having desirable melt characteristics and particularly polyalkylene terephthalate esters, such as polybutylene terephthalate esters in the form of melt extruded pellets, or melt extruded thermoplastic sheet.

The thermoplastic blends of the present invention also can contain other active or inactive fillers, for example, carbon black, fiber glass, chalk, antioxidants, stabilizers, such as salts of lead, cadmium, calcium, zinc, tin, or barium, waxes, dyes, pigments, zinc oxides, etc.

In addition to the above-described thermoplastic blends in pelletized, powder or sheet form, the present invention is also directed to foamed shaped structures derived from the aforementioned blends by conventional injection molding techniques and the like which foamed thermoplastic structures have improved impact strength.

In order that those skilled in the art will be better able to practice the invention, the following examples are given by way of illustration and not by way of limitation. All parts are by weight.

EXAMPLE 1

A dihydrooxidiazinone used as a blowing agent in the preparation of thermoplastic blend as described below and more particularly 5-phenyl-3,6-dihydro-1,3,4-oxidiazin-2-one was prepared as follows:

About 13 parts of bromine was added with stirring to a mixture of 474.6 parts of acetophenone in about 640 parts of methanol, while the mixture was stirred and maintained at a temperature between 5°–10° C. Hydrogen bromide gas was then introduced into the mixture until bromine coloration disappeared, at which point an additional amount of bromine was added over a 2 hour period to make a total of 631.3 parts. There was then added 71 parts of water while the mixture was stirred and externally cooled for a period of about 30 minutes. An excess of about 2700 parts of water was then slowly added to effect the precipitation in the form of crystals of α-bromo acetophenone from the mixture. The crystals were decanted by means of a vacuumed siphon, washed, then neutralized with a 20% sodium hydroxide solution, and decanted to dryness. There was then added about 940 parts water, 1600 parts of methanol, 333 parts of sodium bicarbonate and a sodium formate solution prepared from 161 parts of a 90% formic acid and sufficient sodium hydroxide to neutralize the acid. The mixture was heated at 60° C with vigorous stirring for 7 hours after which time it was cooled to ambient temperature and filtered. Based on method of preparation and gas chromotographic analysis of the mixture, there was produced α-hydroxyacetophenone in quantitative yields.

Dilute hydrochloric acid was added to the mixture of the above filtrate with 855.8 parts of methyl carbazate which had been prepared from equivalent amounts of hydrazine and dimethyl carbonate. Sufficient hydrochloric acid was used to provide a pH of 5.5 after which the mixture was stirred at 38° C for 6 hours. A crystalline precipitate was formed which was filtered from the mixture and washed with water. Based on method of preparation and spectroscopic analysis, the product was the carbomethoxy hydrazone of α-hydroxy acetophenone.

A mixture of the above carbomethoxy hydrazone and about 1,900 parts of toluene was refluxed under reduced pressure to effect the removal of residual water from the crystalline product. There was then added 10 parts of anhydrous potassium carbonate to the mixture and the heating was continued under reduced pressure until all of the methanol-toluene azeotrope was removed. The mixture was then allowed to cool to produce the above-described blowing agent 5-phenyl-3,6-dihydro-1,3,4-oxadiazin-2-one which was finally dried in a vacuum oven at 70°–80° C. The overall yield of final product was 456 parts which represented a 65.5% yield based on acetophenone. The melting point of the product was 163°–165° C.

Dry powder blends of a Bisphenol-A polycarbonate resin powder having an intrinsic viscosity on the average of about 0.55dl/g in chloroform at 25° C and a density of about 1.17 with the above described blowing agent of the present invention and a commercially available blowing agent isopropyl hydrazo dicarboxylate were prepared consisting respectively of 0.6 parts of blowing agent per 100 parts of the polycarbonate resin. The polycarbonate resin was in the form of a finely divided powder which had been dried at 125° C for 16 hours. The aforementioned blends were melt extruded at temperatures in the range of from about 282° C to 305° C. During melt extrusion thermoplastic foam was formed from the aforementioned finely divided dry blends. In addition to melt extruding the aforementioned foamable blends there was also melt extruded the same polycarbonate resin free of blowing agent. The density (g/cc) of the respective blends and the resin free of blend was measured from samples extruded over the range of between 282° C to 305° C. The intrinsic viscosity of the polycarbonate resin and the intrinsic viscosity in chloroform at 25° C of the polycarbonate resin and the aforementioned blends was also measured from samples extruded over the range of between 282° C to 322° C to determine the reduction in molecular weight if any during the foaming process as a result of polymer degradation. The following table shows the result obtained, where "T" is in °C, "Density" shows the change effected over a temperature as a result of "foaming", "IV" shows the change in intrinsic viscosity if any, of the polycarbonate resin as a result of polymer degradation due to by-products of the blowing agent, where Blend A contains the dihydrooxadiazinone in accordance with the present invention and Blend B contains the isopropyl hydrazo-dicarboxylate:

TABLE I

| | Density (g/cc) | | |
|---|---|---|---|
| T(° C) | Polycarbonate | Blend A | Blend B |
| 282 | 1.17 | 1.18 | 1.15 |
| 293 | — | 1.03 | 0.82 |

TABLE I-continued

| T(° C) | | | |
|---|---|---|---|
| 299 | — | — | 0.80 |
| 305 | 1.13 | .86 | 0.70 |
| 316 | 1.14 | — | — |
| 321 | — | — | — |

| | Intrinsic Viscosity (dl/g) | | |
|---|---|---|---|
| T(° C) | Polycarbonate | Blend A | Blend B |
| 282 | 0.57 | 0.57 | 0.55 |
| 293 | 0.56 | 0.57 | — |
| 299 | — | — | 0.48 |
| 305 | 0.54 | 0.53 | 0.46 |
| 316 | 0.54 | — | — |
| 321 | 0.52 | — | — |

The above results show that the molding temperature of the dihydrooxadiazinone of the present invention Blend A is somewhat higher than the molding temperature of the isopropylhydrazodicarboxylate Blend B. More significant, however, is the showing that the blowing agent of the present invention does not significantly change the intrinsic viscosity of the polycarbonate as the result of the foaming action. The polymer extruded with the isopropylhydrazodicarboxylate blowing agent of the prior art shows a 15% decrease in the intrinsic viscosity of the polymer indicating that significant polymer degradation has occurred.

EXAMPLE 2

Various dry blended thermoplastic foamable blends were made with polycarbonate pellets containing 5% glass fibers. The polycarbonate resin used to make the glass filled pellets had a density of about 1.2g/cc. The various blends contained about 0.25 part of blowing agent, per 100 parts of the pellets, and included the dihydrooxadiazinone blowing agent of the present invention as shown in Example 1, also the blowing agent of the prior art, as discussed in Example 1, 5-phenyl-tetrazole, another prior art blowing agent. The various blends were converted to 12 × 12 × ⅜ inches panels using a Siemag Structomat foam injection molding machine. The impact strength of the panels were measured by the falling dart method (ASTM D1709-62T); all of the resulting panels were found to have a density of 0.85 g/cc. The following table shows the impact results obtained from the various panels.

TABLE II

| Blowing Agent | Impact Values (ft.lb.) |
|---|---|
| 5-phenyl-3,6-dihydro-1,3,4-oxadiazin-2-one | > 90 |
| isopropyl hydrazo dicarboxylate | 80 |
| 5-phenyl-tetrazole | 80 |

EXAMPLE 3

The polycarbonate resin blends of Example 2 were converted initially to pellets and thereafter injection molded to test bars to determine Izod Impact Strength (ASTM D256-56). In order to make the test bars from this 5-phenyl tetrazole, it was necessary to injection mold the thermoplastic blend in the form of a pellet-powder mix. The following table shows the results obtained with respect to a comparison of the change in intrinsic viscosity going from the pellets to the bars, as well as the change in unnotched Izod Impact results, where IV is as previously defined:

TABLE III

| Blowing Agent | I.V. (dl/g) | | | Unnotched Izod (ft-lb) |
|---|---|---|---|---|
| | Pellets | Bars | Change | |
| 5-phenyl-3,6-dihydro-1,3,4-oxadiazin-2-one | 0.46 | 0.445 | 3% | 16 |
| isopropylhydrazo carboxylate | 0.46 | 0.390 | 15% | 9.4 |
| 5-phenyl-tetrazole | 0.46 | 0.419 | 10% | 14 |

The above results show that the foamed panels "bars" suffered significant change in intrinsic viscosity as a result of using different blowing agents. The change in the intrinsic viscosity of the polycarbonate also resulted in a change in unnotched izod impact when the isopropylhydrazodicarboxylate was used, as compared to the dihydrooxadiazinone of the present invention. Although 5-phenyl tetrazole did not degrade the polycarbonate as severely as the isopropylhydrazodicarboxylate, it was inherently limited to its use in the form of a dry powder blend since its decomposition temperature was not sufficiently high enough to convert it to pelletized form prior to its conversion to the test panel. This clearly shows that the dihydrooxadiazinone blowing agents of the present invention can offer significant advantages with respect to flexibility and fabrication as well as providing thermoplastic foam products having superior impact strength.

EXAMPLE 4

Extruded concentrates of 5 parts of the dihydrooxadiazinone blowing agent of Example 1, per 100 parts of polycarbonate resin and 5 parts of isopropylhydrazodicarboxylate per 100 parts of polycarbonate resin, where the concentrates were in pelletized form, were respectively mixed with 19 parts, per part of pelletized concentrate, of a polycarbonate resin containing 5% glass fibers. The foamable blends were then foam molded in a Siemag Structomat foam injection molding machine to obtain panels of the dimensions 12 × 12 × ⅜ inches. The density of the panels were 0.85 grams/cc. Impact strength of the panels were measured by the falling dart method (ASTM D1709/62T). The panel derived from the concentrate containing the dihydrooxadiazinone blowing agent had an impact strength which averaged 90 ft.-lbs. The concentrate derived from the isopropylhydrazodicarbonxylate blowing agent provided a panel having an impact strength which averaged only 60 ft.-lb.

EXAMPLE 5

A tumble-blended mixture "Blend C" of 0.6 parts of 5,6-diphenyl-3,6-dihydro-1,3,4-oxadiazin-2-one and per 100 parts of a polyester, VALOX®310, manufactured by the General Electric Company, was extruded over a temperature range of between 235° C to 254° C. The intrinsic viscosity "IV" of the foamed polyester resin extrudate was measured in heptafluoroisopropenol at 25° C to determine the reduction in molecular weight, if any, during the foaming process compared to the unfoamed extruded polyester as a result of polymer degradation. The densities of these extruded' samples were likewise measured. The following table shows the results obtained:

TABLE IV

| T(° C) | Density (g/cc) | | I.V. (dl/g) | |
|---|---|---|---|---|
| | Polyester | Blend C | Polyester | Blend C |
| 235 | — | 0.725 | — | 0.870 |

TABLE IV-continued

| T(° C) | Density (g/cc) Polyester | Density (g/cc) Blend C | I.V. (dl/g) Polyester | I.V. (dl/g) Blend C |
|---|---|---|---|---|
| 238 | 1.282 | 0.725 | 0.925 | 0.917 |
| 243 | — | 0.723 | — | 0.930 |
| 249 | 1.292 | 0.765 | 0.860 | 0.941 |
| 254 | — | 0.758 | — | 0.945 |

The above results show that the dihydrooxadiazinone effects very good density reduction; more significant is the blowing agent of the present invention does not significantly lower the intrinsic viscosity of the polyester resin as a result the foaming action indicating little or no polyester degradation.

EXAMPLE 6

A blend was prepared using 15 parts of 5,6-diphenyl-3,6-dihydro-1,3,4-oxadiazin-2-one and 85 parts of Hytrel®4056 a polyester-polyether-copolymer which was extruded into pellets on a Brabender instrument under the following conditions: die temperature, 200° C; middle zone, 139° C; back zone, 188° C. The extruded material showed no evidence of bubbling.

The above polyester-polyether-copolymer containing 15% of the dihydroxadiazinone is used as a blowing agent concentrate for the foaming of polyesters such as poly(butyleneterephthalate) by tumble mixing 1 part of the blowing agent concentrate per 39 parts of the polyester resin and foam molding this mixture under the following conditions: rear temperature, 243° C; center, 254° C; front, 240° C; mold, 93° C. A density reduction in the molded part of 35% is observed.

EXAMPLE 7

A tumble-blended mixture of 0.7 part of 5-phenyl-3,6-dihydro-1,3,4-oxadiazin-2-one per hundred parts of P-1700 polyarylsulfone manufactured by the Union Carbide Corporation was foam molded into plaques having the dimensions 3⅜ by 3¼ by ⅜ inches on a Battenfeld BSKM 70/100B injection molding machine under the following conditions: rear temperature, 299° C; center 302° C; front, 310° C; mold, 82° C. The foamed plaque had a density of 0.51 g/cc whereas an identical plaque without the blowing agent had a density of 1.27 g/cc.

EXAMPLE 8

A tumble-blended mixture of 0.7 parts of 5-phenyl-3,6-dihydro-1,3,4-oxadiazine-2-one per 100 parts of an acrylonitrile-butadiene-styrene (ABS) copolymer was foam molded into plaques as in Example 7 under the following conditions: rear temperature, 260° C; center, 290° C; front, 288° C; mold, 38° C. The foamed plaque had a density of 0.60 g/cc whereas an identical plaque without a blowing agent had a density of 0.99 g/cc.

EXAMPLE 9

A tumble-blended mixture of 0.7 part of 5-phenyl-3,6-dihydro-1,3,4-oxadiazin-2-one, per 100 parts of a polymer alloy of polyphenylene oxide and polystyrene was foam molded into plaques as in Example 8 under the following conditions: rear temperature, 293° C; center, 299° C; front, 304° C; mold, 49° C. The foamed plaque had a density of 0.56 g/cc whereas an identical plaque without a blowing agent had a density of 1.07 g/cc.

EXAMPLE 10

A tumble-blended mixture of 0.5 part of 5,6-diphenyl-3,6-dihydro-1,3,4-oxadiazin-2-one, per 100 parts of a hexamethylene diamine-adipic acid polyamide resin was foam molded as in Example 7 under the following conditions: rear temperature, 238° C; center, 249° C; front, 252° C; mold, 52° C. The foamed plaque had a density of 0.53 g/cc whereas an identical plaque without a blowing agent had a density of 1.01 g/cc.

EXAMPLE 11

A tumble-blended mixture of 0.7 part of 5,6-diphenyl-3,6-dihydro-1,3,4-oxadiazin-2-one per 100 parts of polypropylene is foam molded as in Example 7 under the following conditions: rear temperature, 180° C; center, 220° C; front, 230° C; mold, 25° C. The foamed plaques have a density in the range of 0.5–0.7 g/cc whereas identical plaques without a blowing agent has a density of 0.95 g/cc.

EXAMPLE 12

A tumble-blended mixture of 0.7 part of 5,6-diphenyl-3,6-dihydro-1,3,4-oxadiazin-2-one per 100 parts of high impact polystyrene was foam molded as in Example 7 under the following conditions: rear temperature, 220° C; center, 249° C; front, 260° C; mold, 38° C. The foamed plaque had a density of 0.68 g/cc whereas an identical plaque without a blowing agent had a density of 1.04 g/cc.

EXAMPLE 13

A slurry is prepared by adding 10 parts of powdered 5-phenyl-3,6-dihydro-1,3,4-oxadiazin-2-one to a solution of 10 parts of isotactic polystyrene having a molecular weight of 200,000 and 80 parts of methylene chloride. The slurry is rapidly mixed and fed to the nozzle of a spray drier. The slurry is injected into a chamber through which air heated to 70° C is circulated. Small granules having a mesh size ranging from 100–200 are collected and dried in a vacuum oven at 50° C. The granules thus obtained are dihydrooxadiazinone encapsulated in polystyrene consisting of 1 part polystyrene to about 1 part of the dihydrooxadiazinone.

One part of this encapsulated blowing agent is then tumble-blended with 99 parts of Bisphenol-A polycarbonate resin and foam molded as in Example 7 under the following conditions: rear temperature, 540° C; center, 575° C; front, 570° C; mold, 95° C. The foamed plaque has a density of 0.85 g/cc whereas an unfoamed plaque has a density of 1.19 g/cc.

EXAMPLE 14

A tumble-blended mixture of 0.7 parts of 5,6-diphenyl-3,6-dihydro-2,3,4-oxadiazin-2-one per 100 parts of Hytrel® 4056, a polyester-polyether copolymer, was foam molded into plaques as in Example 7 under the following conditions: rear temperature, 226° C; center, 238° C, front, 249° C; mold, 25° C. The foamed plaque had a density of 0.68 g/cc whereas an identical plaque without the blowing agent had a density of 1.13 g/cc.

EXAMPLE 15

A synthesis of 1,1-dichloro-2,2-bis(4-hydroxyphenyl) ethylene based on the dehydrochlorination of S. Porejko and Z. Wielgosz, "Synthesis and Properties of Polycarbonates with Chloro Bisphenols", Polymer 13, (2) 55, (1968).

A mixture of 26.25 parts of 1,1-dichloro-2,2-bis (4-hydroxyphenyl)ethylene, 0.026 part of sodium gluconate, 0.237 part of phenol, 0.142 part of triethylamine, 123 parts of methylene chloride and about 75 parts of water is stirred for about 10 minutes at a temperature of about 28° C. There is then added to the mixture, an aqueous sodium hydroxide solution in an amount to adjust the pH of the aqueous phase of the mixture to approximately 10.

While the mixture is being thoroughly agitated, phosgene is introduced at a rate of about 12.24 parts per hour while a 20% aqueous sodium hydroxide solution is added in an amount sufficient to maintain the pH of the aqueous phase of the mixture at 10. Phosgenation of the mixture is continued for about ¾ of an hour under these conditions and then the rate of phosgenation is reduced to about 6.8 parts per hour while maintaining the pH of the aqueous phase to a range of about 11 to 11.5. The phosgenation of the mixture is then continued for about 50 minutes.

The above reaction mixture is then diluted with about 100 parts of methylene chloride, and washed alternatively with dilute hydrochloric acid, dilute sodium hydroxide and water. The mixture is then centrifuged and filtered and thereafter steam precipitated. There is obtained 26 pounds of product after the precipitate is recovered and dried at 80° C. Based on method of preparation, the product is 1,1-dichloro-2,2-bis(4-hydroxyphenyl) ethylene polycarbonated having an intrinsic viscosity of 0.51 dl/g in chloroform at 25° C.

The above described dichloroethylene polycarbonate is blended with 5-phenyl-3,6-dihydro-1,3,4-oxidiazin-2-one and glass fiber to produce a blend having .5% by weight of blowing agent and 5% by weight of glass fiber. The mixture is then melt extruded into pellets at 500° F.

In accordance with ASTM-E-162-67, 6 × 18 × ¼ inches test panels are prepared by foam molding the above blend from the above described pellets at 575° F. This material has a Gardner Impact Value of about 25–37.5 ft/lb and a density of about 1.07. Equivalent test panels are also prepared from a blend of the above-described dichloroethylene polycarbonate and 5% by weight of glass fiber free of blowing agent. The test panels are then used in evaluating the flame retardant properties of the glass filled dichloroethylene polycarbonate and the rigid foam derived therefrom in accordance with ASTM-E-162-67. It is found that the unfoamed test panel has an $I_s$ value of 0 which is equivalent to asbestos. The foamed panel is found to have an $I_s$ value of 0.8 indicating the foaming of the original dichloroethylene polycarbonate glass fiber blend does not significantly reduce the flame retardant properties of the original blend.

EXAMPLE 16

A blend is prepared of about equal parts by weight of the dichlorothylene polycarbonate of Example 15, and a Bisphenol-A polycarbonate having an intrinsic viscosity of about 0.55 dl/g in chloroform at 25° C, along with 5% by weight of the total of glass fiber and 0.5% by weight of the blowing agent of Example 15. The blend is melt extruded into pellets at 500° F. Pellets are also prepared from the same blend free of blowing agent.

A 6 × 18 inches test panel is prepared following the procedure of Example 15 by foam molding the blend at 600° F. The foamed blend has an $I_s$ value of 3.9 which is substantially equivalent to the superior flame retardant 3.7 value for the unfoamed blend. The foamed blend also has an intrinsic viscosity of about 0.45 dl/g in chloroform at 25° C, a Gardner Impact Value greater than 50 ft-lb and a density of about 1.

EXAMPLE 17

A blend of 75 parts of the dichloroethylene polycarbonate of Example 15 and 25 parts of an ABS resin is pelletized at 500° F with 0.5% by weight of the blend of the blowing agent of Example 15 and 5% by weight of glass fiber.

Test panels are prepared by foam molding the blend at 575° F. A comparison of $I_s$ values between foamed and unfoamed 6 × 18 × ¼ inches test panels in accordance with ASTM-E-162-67 shows a 12.0 for the unfoamed panel and a 12.5 for the foamed panel.

EXAMPLE 18

A copolymer of 1,1-dichloro-2,2-bis(4-hydroxyphenyl)ethylene and 2,2-bis(4-hydroxyphenyl)propane (Bisphenol-A) is prepared in accordance with the procedure of Example 15 using 13.12 parts of the dichloroethylene bisphenol and 10.65 parts of Bisphenol-A.

The above described copolymer is pelletized with 5-phenyl-3,6-dihydro-1,3,4-oxidiazin-2-one and glass fiber as in Example 15.

It is found that the $I_s$ value of the unfoamed panel is 3.8 while the foamed panel has an $I_s$ of 4.0.

As shown above in Examples 15–18, which correspond to Examples 1, 2, 4 and 5 of my copending application Ser. No. 669,027, filed Mar. 22, 1976, filed concurrently herewith and assigned to the same assignee as the present invention, certain foams derived from particular compositions of the present invention, provide spectacular radiant panel test values, or $I_s$ values as described by ASTM-E-162-67. The $I_s$ values shown by the foams of RD-8142, readily satisfy the requirements of UL Bulletin 484, and can be readily distinguished from thermoplastic foams of the prior art. The thermoplastic foams of Ser. No. 669,027, filed Mar. 22, 1976 are derived from the melt of thermoplastic organic blends having at least 5% by weight of chemically combined haloalkylene polycarbonate units of the formula

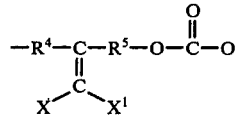

where $R^4$ and $R^5$ are the same or different divalent aromatic radicals having from 6–13 carbon atoms, X is a halogen atom, and $X^1$ is selected from X and hydrogen. The thermoplastic organic blends can be reinforced with up to 60% by weight of glass fiber; the blends also can consist of haloalkylene polycarbonate, blends of such haloalkylene polycarbonate with other thermoplastic polymers previously defined or a copolymer of the above haloalkylene carbonate units with other bisphenol carbonate units.

Although the above examples are limited to only a few of the thermoplastic organic polymers and dihydrooxadiazinones which can be used in the practice of the present invention, it should be understood that the present invention is directed to foamable compositions comprising the dihydrooxadiazinones of formula 1 and the thermoplastic organic polymers described prior the these examples. In addition, the present invention is directed to a method of making a foamed structure at temperatures between about 170° C to 400° C by injection molding foamable compositions as previously in the form of pellets, or powder mixtures or with the use of blends of dihydrooxadiazinone concentrates or in encapsulated foam with additional amounts of thermoplastic organic polymers. The term thermoplastic organic polymer as previously defined includes polycarbonates having chemically defined

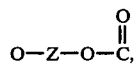

where Z is selected from the class consisting of $R^6$ and $R^6$-Q-$R^6$, where $R^6$ is a divalent aromatic radical having from 6–13 carbon atoms and Q is selected from the class consisting of,

divalent cycloaliphatic radicals, oxyaryleneoxy radicals, sulfonyl, sulfinyl, oxy, thio, fluorenyl, phenolphthalein and $R^7$ is selected from the class consisting of $C_{(1-8)}$alkyl, $R^6$ and halogenated derivatives.

What I claim as new and desire to secure by Letters Patent of the United States is:

1. A substantially uniform injection moldable foamable blend comprising thermoplastic organic polymer and from 0.1% to 25% by weight of 5-phenyl-3,6-dihydro-1,3,4-oxadiazin-2-one.

2. An injection moldable concentrate in accordance with claim 1, having from 1% to 25% by weight of 5-phenyl-3,6-dihydro-1,3,4-oxadiazin-2-one.

3. A substantially uniform injection moldable blend in accordance with claim 1 comprising a thermoplastic organic polymer and 0.1 to 1.0% of 5-phenyl-3,6-dihydro-1,3,4-oxadiazin-2-one, which blend is convertible to a substantially uniform thermoplastic foam under molding conditions.

4. A blend as in claim 3, in the form of a dry powder mixture of finely divided resinous thermoplastic organic polymer and 5-phenyl-3,6-dihydro-1,3,4-oxadiazin-2-one blowing agent.

5. A blend as in claim 3, in the form of pellets of thermoplastic polymer coated with 5-phenyl-3,6-dihydro-1,3,4-oxadiazin-2-one blowing agent.

6. A blend as in claim 3, in the form of thermoplastic pellets.

7. A blend as in claim 3, in the form of a thermoplastic sheet.

8. A blend as in claim 1, in which the 5-phenyl-3,6-dihydro-1,3,4-oxadiazin-2-one is encapsulated.

9. A blend in accordance with claim 1, where the dihydrooxadiazinone is 5-phenyl-3,6-dihydro-1,3,4-oxadiazin-2-one.

10. A blend in accordance with claim 1, where the dihydrooxadiazinone is 3,6-dihydro-5,6-diphenyl-1,3,4-oxadiazin-2-one.

11. A blend in accordance with claim 1, where the thermoplastic organic polymer is a polycarbonate of 2,2-bis-(4-hydrophenyl)-propane.

12. A blend in accordance with claim 1, where the thermoplastic organic polymer is a polyalkylene(-terephthalate).

13. A blend in accordance with claim 1, where the thermoplastic organic polymer is polyphenyleneoxide based resin.

14. A substantially uniform injection moldable foamable blend comprising a 5-phenyl-3,6-dihydro-1,3,4-oradiazin-2-one and thermoplastic organic polymeric material having at least 5% by weight of chemically combined haloalkylene polycarbonate units of the formula,

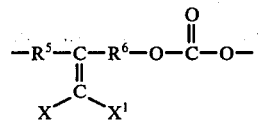

where $R^5$ and $R^6$ are the same or different divalent aromatic radicals having from 6–13 carbon atoms, X is a halogen atom and $X^1$ is selected from X and hydrogen.

15. A blend in accordance with claim 14, where the organic polymeric material is a polycarbonate consisting essentially of 1,1-dichloro-2,2-bis(4-hydroxyphenyl)ethylene carbonate units.

16. A blend in accordance with claim 14, where the organic polymeric material is a copolymer consisting essentially of chemically combined 1,1-dichloro-2,2-bis(4-hydroxyphenyl)ethylene carbonate units and 2,2-bis(4-hydroxyphenyl)propane carbonate units.

17. A glass fiber reinforced blend in accordance with claim 14.

18. A foamable composition in accordance with claim 14, where the organic polymeric material is a blend of a haloethylene polycarbonate and an acrylonitrile-butadiene-styrene terpolymer.

19. A foamable composition in accordance with claim 14, where the organic polymeric material is a blend of a haloethylene-bisphenol polycarbonate and an isopropylidene-bisphenol polycarbonate.

20. Thermoplastic pellets comprising a 2,2-bis (4-hydroxyphenyl)propane polycarbonate resin and about 0.1 to 1.0% by weight of 5-phenyl-3,6-dihydro-1,3,4-oxadiazin-2-one, based on the weight of the pellets.

21. Thermoplastic pellets consisting essentially of a polyalkylene terephthalate and about 0.1 to 1.0% by weight of 3,6-dihydro-5,6-diphenyl-1,3,4-oxadiazine-2-one based on the weight of the pellets.

22. A substantially uniform injection moldable foamable blend comprising thermoplastic organic polymer and 0.1% to 25% by weight of a dihydrooxadiazinone, where the thermoplastic organic polymer is selected from the class consisting of polyalkylene terephthalates, polycarbonates, polyamides, polyester-polyether copolymers, polycarbonate copolymers and blends thereof.

23. An injection moldable concentrate in accordance with claim 22, having from 1% to 25% by weight of the dihydro-oxadizinone.

24. A substantially uniform injection moldable blend in accordance with claim 22 comprising a thermoplastic organic polymer and 0.1 to 1.0% of a dihydrooxadiazinone, which blend is convertible to a substantially uniform thermoplastic foam under molding conditions.

25. A blend as in claim 24, in the form of a dry powder mixture of finely divided resinous thermoplastic organic polymer and dihydrooxadiazinone blowing agent.

26. A blend as in claim 24, in the form of pellets of thermoplastic polymer coated with dihydrooxadiazinone blowing agent.

27. A blend as in claim 24, in the form of thermoplastic pellets.

28. A blend as in claim 24, in the form of a thermoplastic sheet.

29. A blend as in claim 22, in which the dihydrooxadiazinone is encapsulated.

30. A blend in accordance with claim 22, where the thermoplastic organic polymer is a polycarbonate of 2,2-bis-(4-hydroxyphenyl)-propane.

31. A blend in accordance with claim 22, where the thermoplastic organic polymer is a polyalkylene(terephthalate).

32. A blend in accordance with claim 22, where the thermoplastic organic polymer is a polyphenyleneoxide based resin.

* * * * *